US007297344B1

(12) United States Patent
Fleischer et al.

(10) Patent No.: US 7,297,344 B1
(45) Date of Patent: Nov. 20, 2007

(54) PREPARATIONS FOR THE PROMOTION OF WOUND HEALING IN THE UPPER RESPIRATORY TRACT AND/OR EAR

(75) Inventors: Wolfgang Fleischer, Ingelheim (DE); Karen Reimer, Hambach (DE)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/701,220

(22) PCT Filed: May 27, 1999

(86) PCT No.: PCT/EP99/03677

§ 371 (c)(1),
(2), (4) Date: Nov. 27, 2000

(87) PCT Pub. No.: WO99/60998

PCT Pub. Date: Dec. 2, 1999

(51) Int. Cl.
*A61K 9/127* (2006.01)

(52) U.S. Cl. .................................... 424/450
(58) Field of Classification Search ............ 424/450, 424/45–47, 489
See application file for complete search history.

(56) References Cited

U.S. PATENT DOCUMENTS

| | | | |
|---|---|---|---|
| 2,706,701 A | 4/1955 | Beller et al. ............... 167/70 |
| 4,113,857 A | 9/1978 | Shetty ..................... 424/150 |
| 4,235,871 A | 11/1980 | Papahadjopoulos et al. .. 424/19 |
| 4,560,678 A | 12/1985 | Ranson ................... 514/44 |
| 4,675,009 A | 6/1987 | Hymes et al. ............. 604/304 |
| 4,906,476 A | 3/1990 | Radhakrishnan ........... 424/450 |
| 4,938,965 A | 7/1990 | Shek et al. ............... 424/450 |
| 5,034,228 A | 7/1991 | Meybeck et al. .......... 424/401 |
| 5,049,388 A * | 9/1991 | Knight |
| 5,049,389 A * | 9/1991 | Radhakrishnan |
| 5,114,928 A | 5/1992 | Gajdos et al. ............. 514/25 |
| 5,128,139 A | 7/1992 | Brown et al. .............. 424/450 |
| 5,232,692 A | 8/1993 | Isenberg et al. ......... 424/78.04 |
| 5,246,708 A | 9/1993 | von Borstel et al. ...... 424/450 |
| 5,290,540 A * | 3/1994 | Prince |
| 5,456,923 A | 10/1995 | Nakamichi et al. ........ 424/489 |
| 5,552,158 A | 9/1996 | Evans et al. ............... 424/450 |
| 5,942,245 A | 8/1999 | Katinger et al. |

FOREIGN PATENT DOCUMENTS

| | | |
|---|---|---|
| CA | 2204 493 | 5/1996 |
| EP | 0260241 | 3/1988 |
| EP | 0317405 | 5/1989 |
| EP | 0404028 | 1/1991 |
| EP | 0509338 | 10/1992 |
| EP | 0613685 | 9/1994 |
| EP | 0639373 | 2/1995 |
| EP | 1013269 | 6/2000 |
| EP | 1013269 A1 | 6/2000 |
| JP | 0-24640 | 2/1989 |
| JP | 2204413 | 8/1990 |
| JP | 7-145081 * | 6/1995 |
| JP | 63126820 | 5/1998 |
| WO | 85/00112 * | 1/1985 |
| WO | 8809165 | 12/1988 |
| WO | 9324165 | 12/1988 |
| WO | 9011781 | 10/1990 |
| WO | 9324165 | 12/1993 |
| WO | 9414490 | 7/1994 |
| WO | 9428876 | 12/1994 |
| WO | 9614083 | 5/1996 |
| WO | 9960999 | 12/1999 |
| WO | 9961003 | 12/1999 |
| WO | 0072823 | 12/2000 |

OTHER PUBLICATIONS

Chemical Abstracts, vol. 117, No. 10 (Sep. 7, 1992); Abstract No. 97244, Brian E. Gilbert et al., *Aerosolized Liposomal Amphotericin B for Treatment of Pulmonary and Systemic Cryptococcus Neoformans Infections in Mice*, 36(7) Antimicrob. Agents Chemotherapy 1466-71 (1992).
Jenny Liautard, et al. "Encapulation of Drugs Into Large Unilamellar Liposomes Prepared by an Extempsaneous Method," J. Microencapsulation, 1991, vol. 8, No. 3, 381-89.
Abstract JP 22 04413 and JP 63-126 820 (English).
P. Wüzler, et al., "Virucidal and Chalmudicidal Activites of Povidone-Iodine (PVP-I) Lipsomes," Clin Microbial Inf 5(suppl 3) 136 (1990) 9th European Conference of Clin Microbiology and Infectious Diseases, Berlin, Mar. 1999.
Bernhard Müllinger, et al., "Coated Drug Droplets Allow Individual Dosimetry," Respiratory Drug Delivery VI, Hilton Head, S.C. May 3-7, 1998, pp. 385-387.
James F. Fitzgerald, et al., "Novel Coating For Improved Pulmonary Drug Delivery," U. Of Florida Office of Graduate Research, Technology and Education, VF#1887, Jan. 15, 1998 (ABSTRACT).
David A. Edwards, et al., "Large Porous Particles for Pulmonary Drug Delivery," Science, vol. 276, Jun. 20, 1997, p. 1868-1871.
H. Schreier, et al., "Formulation and in-vitro performance of liposome powder aerosols," S.T.P. Pharma Sciences 4(1) 38-44, 1994.
Hans Schreier, et al., "Pulmonary delivery of liposomes ," Journal of Controlled Release, 24 (1993) 209-223.
Abstract EP 0613685 (English).
Abstract EP 0509338 (English).
Janine F. Bridges, et al., "The Uptake of Liposome-Entrapped I-Labelled Poly(Vinyl Pyrrolidone) By Rat Jejunum In-Vitro," Biochemica et Biophycica Acta, 544 (1978) 448-451.
Peter M. Vogt, et al. "Polyvinyl pyrrolidone-iodine Lipsome Hydrogel Improves Epithelialization By Combing Moisture And Antisepsis. A New Concept In Wound Therapy," Wound Repair and Regeneration vol. 9 No. 2 p. 116-122.

(Continued)

Primary Examiner—Gollaamudi S. Kishore
(74) Attorney, Agent, or Firm—Jones Day

(57) ABSTRACT

Use of anti-inflammatory agents such as povidone iodine for the preparation of a pharmaceutical composition for the treatment of diseases of the upper respiratory tract and/or the ear which are susceptible to the administration of such agents.

25 Claims, No Drawings

OTHER PUBLICATIONS

Karen Reimer, et al., "*An Innovative Topical Drug Formulation for Wound Healing And Infection Treatment: In-Vitro and In-Vivo Investigations of a Povidone-Iodine Liposome Hydrogel*," Dermatology 2000, 201: 235-241.

Xiaonan Cia, 1994, "The Clinical Use and Dosage Form of Iodophors", Bulletin of the Medical School of Shantou University (2):77.

Ganzer et al., 2001, Arthroskopie 14:31.

Lineaweaver et al., 1985, Arch Surg 120:257-270.

Kallengerger et al., 1991, Hyg+Med 16:383-395.

Weiner et al., 1989, Drug Development and Industrial Pharmacy, 15 (10), 1523-1554.

Vogt et al., 2001, Wound Rep. Reg. 9:116-122.

Reimer et al., 2000, Dermatology 201:235-241.

Integrated Final Study Report for HOM3401.

\* cited by examiner

PREPARATIONS FOR THE PROMOTION OF WOUND HEALING IN THE UPPER RESPIRATORY TRACT AND/OR EAR

The invention concerns preparations for the application of agents with anti-inflammatory, especially antiseptic and/or wound healing promoting properties to the upper respiratory tract and/or the ear. The preparations are specifically applied to wounds, skin, mucous membranes and mucosa-like unkeratinized epithelial, especially ciliary epithelial tissues in the upper respiratory tracts and/or the ears of humans and animals.

Furthermore, the invention concerns a method of preventing or treating infections by applying a pharmaceutical preparation.

A plurality of different antibiotic and antiseptic agents are known for the topical treatment of infectious maladies. A decisive disadvantage of antibiotic agents is that the infecting bacteria show primary resistances, and can acquire secondary resistances, against these agents. Further, antibiotics quite often lead to patient sensibilisation. The use of e.g. halogen-releasing antiseptics such as povidone iodine, also known as polyvidone iodine or PVP-iodine, i.e. the poly(1-vinyl-2-pyrrolidin-2-one)-iodine complex, can prevent resistances. Antiseptic agents are also much more rarely allergenic as compared to antibiotics.

At present, infectious diseases of the respiratory tract are treated with antibiotics. The application of antibiotic agents via the respiratory tract has been the subject of several reviews and articles with an emphasis, however, on the lower respiratory tract. Ramsey et al., for example, describe the intermittent administration of inhaled tobramycin in patients with cystic fibrosis in "The New England Journal of Medicine", Volume 340, Number 1, 1999, p. 23-30.

The aerosolization of imipenem/cilastatin for preventing pseudomonas-induced acute lung injury has been investigated by Wiener-Kronish in "Journal of Antimicrobiol Chemotherapy" (1996) 38, p. 809-818.

Pulmonary applications of different antibiotic agents, like benzyl penicillin, tobramycin or amikacin, for the treatment of infectious diseases are described by Schreier in several recent reviews, e.g. in "Medical applications of liposomes", Papahadjopoulos and Lasic (eds.), Elsevier 1998.

However, the treatment with antibiotics leads to the complications known to the skilled person. For example, patients suffering from acute or chronic laryngopharyngitis are often treated with antibiotics in order to alleviate the symptoms. This often merely leads to resistances of the bacteria responsible for the symptoms. Many diseases of the respiratory tract are caused by viruses. One typical example, in the upper respiratory tract, is rhinitis. Antibiotics are inefficient in such cases, and such patients are not cured of the infections.

The use of antiseptics and/or wound-healing promoting agents for external application to humans and animals is disclosed in our earlier patent EP 0 639 373. Specifically, liposome preparations of PVP-iodine are shown therein to be topically applicable to the external parts of the eye. These preparations generally take the form of a cream, an ointment, a lotion, a gel or a drop formulation.

Liposomes are well-known drug carriers and therefore the application of medicaments in liposomal form has been subject of investigation for quite some time. An overview concerning pulmonary delivery of liposome encapsulated drugs in asthma therapy is provided by the review "Pulmonary delivery of liposomes" (H. Schreier, in "Journal of Controlled Release", 24, 1993, p. 209-223). The physicochemical characterization of liposome aerosols and also their therapeutic applications to the respiratory tract are shown therein. Drugs that have been investigated for pulmonary delivery via liposomes include, e.g. anti-cancer agents, peptides, enzymes, anti-asthmatic and anti-allergic compounds and, as mentioned above, also antibiotics. The formulation of liposome aerosols or liposome powder aerosols using, for example a dry powder inhaler has also been described by H. Schreier in "Formulation and in vitro performance of liposome powder aerosols" (S.T.P. Pharma Sciences 4, 1994, p. 38-44).

Although a lot of attention has been paid to liposomes as drug carriers, as can be seen from the cited documents, there appears to be no prior art relating to liposomes and other particulates as carriers of anti-inflammatory, especially antiseptic and/or wound-healing promoting agents for applications in the body, especially in the upper respiratory tract, including the mouth, throat and nose, and in the ear.

Most of the prior art cited above is concerned with liposome preparations. It should be understood that alternative drug carriers of a similarly particulate character exist. These drug carriers can often—and also in the context of this invention—be used instead of liposomes and include microspheres (generally comprising lipophilic polymers), nanoparticles, "Large Porous Particles" and individually coated drug substance molecules, e.g. made by using pulsed laser deposition (PLD) techniques. These PLD methods can be used to apply coatings to drug powders and to modify surface properties and release rate to a variety of drug systems.

Where hereinafter reference is made to liposomes or particulate carriers, it is to be understood that this is to incorporate such alternative carriers, too.

It is known in the art that the administration of inhalable particles to the respiratory tract can be achieved by nebulization or aerosolization of the liposome, microsphere, Large Porous Particle, PLD or nanoparticle preparations or by dry powder inhalation of the respective preparation.

There appears to be a marked reluctance in the art, to apply disinfectants to interior parts of the body, except maybe in extreme cases of life-threatening septical complications.

Generally, antibiotic preparations appear to be preferred, even in view of their above-discussed disadvantages.

An object of the instant invention is to provide a well tolerated, easily applicable, anti-inflammatory, especially antiseptic and/or wound-healing promoting preparation, which provides protracted release and protracted topical effect of the active agent in the upper respiratory tract.

According to the invention this object is attained in that the preparation comprises at least one anti-inflammatory, especially antiseptic and/or wound healing promoting agent in the form of a particulate carrier preparation, as defined in independent claim 1.

The invention further comprises a method of treating the upper respiratory tract, in humans and animals, as defined in independent claim 25.

The dependent claims define further advantageous embodiments of the invention.

In the context of the invention, the upper respiratory tract is considered to broadly include the mouth, nose and throat areas, down to and including the larynx and excluding the external facial skin areas of mouth and nose. The upper respiratory tract thus comprises those parts which may be considered to be inside the body. In the same context, the ear is considered to broadly include those parts of the ear which lie inside the skull, but are accessible from the outside thereof. Generally, this will include the passages of the outer ear and, in some cases, the middle ear, but will exclude the inner ear and also those parts of the outer ear which surround the ear orifice, on the outside of the skull.

In the context of this invention, anti-inflammatory agents are understood to include antiseptic agents, antibiotic agents, corticosteroids, and wound-healing agents, as defined below.

In the context of this invention, antiseptic agents are understood to include those disinfecting agents which are pharmaceutically acceptable and suitable for the treatment of the upper respiratory tract to the extent that they can be formulated in accordance with the invention.

More specifically, antiseptic agents include inter alia oxygen- and halogen-releasing compounds; metal compounds, e.g. silver and mercury compounds; organic disinfectants including inter alia formaldehyde-releasing compounds, alcohols, phenols including alkyl- and arylphenols as well as halogenated phenols, quinolines and acridines, hexahydropyrimidines, quaternary ammonium compounds and iminium salts, and guanidines.

Wound-healing agents comprise agents promoting granulation and epithelization such as dexpanthenol, allantoines, azulenes, tannines, and vitamin B-type compounds.

The invention is premised on the surprising fact that particulate carriers, especially liposomes, but also microspheres, nanoparticles and coated drug substance molecules, are highly suited as carriers for antiseptic agents, especially for povidone iodine, and for agents promoting the healing of wounds, for application to the upper respiratory tract.

The preparations according to this invention permit protracted release of the agent or agents, and provide an extended and topical activity at the desired locus of action by interaction with cell surfaces.

The invention is, another aspect, based on a further surprising and unexpected fact. It is well known in the art that the formation of new body tissues may cause problems. Thus, it is known that body tissue repair may be accompanied by the formation of scar tissue, which can be functionally and/or cosmetically harmful, or at least undesirable. Hyperkeratosis and the uncontrolled proliferation of tissue may cause serious harm, leading to dysfunctions, and may of course also be cosmetically undesirable. After infections and inflammations, re-growing or healing tissue may cause neoplasms and intergrowth. It is thus well known in the art that in the curing of diseases, proper remodelling of tissue is not only desirable, but in fact necessary.

It has now been surprisingly found that the use of anti-inflammatory agents, singly or in combination with other such agents, leads to markedly less formation of undesirable body tissue in the course of tissue repair and other tissue growth processes. Thus, the formation of scar tissues is reduced, in skin but also in mucosa and in other tissues, such as muscle or inner organ tissues. Hyperkeratosis may be entirely suppressed, and intergrowth, or neoplasm formation in the curing of infective diseases is also highly reduced.

One object achieved by the invention is therefore concerned with improved tissue repair in the body. The invention achieves this by the application of anti-inflammatory agents, in the form of a particulate carrier preparation as defined in the independent claims.

The anti-inflammatory, antiseptic and/or wound-healing preparation can be administered to the respiratory tract by a nebulization agent loaded of the particulate carrier preparation, or by dry powder inhalation of the respective preparation. For example, a liposome preparation can be made by loading liposomes with PVP iodine in a conventional procedure.

It is also possible to compact the loaded liposomes, optionally together with auxiliary materials, such as low molecular sugars, preferably lactose, to a tightly compacted solid medicament reservoir. This medicament stock can then be abraded or micronized or treated in other ways to yield the powder in particle form. The resulting liposome preparation can be administered by inhalation of the preparation in the form of a powder aerosol, as, for example, described in "Acute Effects of Liposome Aerosol Inhalation on Pulmonary Function in Healthy Human Volunteers" (Thomas et al., Preliminary report, Volume 99, 1991, p. 1268-1270). The pressures for preparing the tightly compacted solid medicament stock are preferably in the range of from 50-500 MPa. Such medicament stock is described in WO 94/14490 and a device for administration is disclosed in WO 93/24165.

The nature or constitution of the liposomes is generally not critical. The liposome preparation as, for example, described in EP 0 639 373 can be administered to the nose or the throat as an aerosol, e.g. a pump spray. For applications in the mouth cavity, the inventive preparations are preferably formulated as a pump spray, a gel, or a rinsing solution. The disclosure of EP 0 639 373 is incorporated by reference.

The preparations according to this invention apparently do not only contain the active agent, like povidone iodine, encapsulated in the particulate carrier, especially in liposomes. It seems that there is also some amount of agent which is not contained inside the carrier. The preparations according to the invention often show a marked initial effect which is observed in addition to the slower, protracted release of the active agent from the carrier. This effect is especially observed where the carrier comprises liposomes. Without wishing to be bound to any theoretical explanation, it is presently assumed that in addition to active agent encapsulated inside the liposomes, some active agent is present outside of the liposomes, and probably loosely bound to the outer surfaces of the liposomes. This could be due to association of active agent molecules with the liposomal membrane, or it could be due to active agent molecules forming a layer on the liposomal surface, which layer partly or even fully coats the liposome externally. The type and amount of this initial agent effect can e.g. be influenced by choice of the concentration parameters.

The amphiphilic substances generally known in prior art to form liposome membranes can be employed in the context of the invention as long as they are pharmaceutically acceptable for the intended application. Presently, liposome forming systems comprising lecithin are preferred. Such systems can comprise hydrogenated soy bean lecithin besides cholesterol and disodium succinate-hexahydrate; it is presently specifically preferred to use hydrogenated soy bean lecithin as the sole membrane-forming agent.

The known prior art methods for forming liposome structures are described in the documents cited above and can generally be used in the context of the invention. Broadly, these methods comprise mechanical agitation of a suitable mixture containing the membrane forming substance and water or an aqueous solution. Filtration through suitable membranes is preferred in forming a substantially uniform liposome size.

The average size of the liposomes according to this invention can vary over a broad range, generally from about 1 to about 20,000 nm. Liposomes with diameters in the range of about 50 and 4,000 nm are preferred. Liposomes with diameters at around 1000 nm are presently most preferred for e.g. gel applications. For solutions, smaller average diameters may be more suitable.

Where alternative particulate carriers are used, they are generally prepared as known in the art. Thus, microspheres which are used to deliver a very wide range of therapeutic or cosmetic agents, are made as described for example in WO 95/15118.

Nanoparticles may in some case be used, provided that they can be loaded with a sufficient amount of active agent and can be administered to the upper respiratory tract according to this invention. They can be prepared according to the methods known in the art, as e.g., described by Heyder (GSF München) in "Drugs delivered to the lung, Abstracts IV, Hilton Head Island Conference, May 1998.

Methods using a pulse laser deposition (PLD) apparatus and a polymeric target to apply coatings to drug powders in a short non-aqueous process are also suitable for the formation of particulate preparations according to this invention. These have e.g. been described by Talton et al., "Novel Coating Method for Improved Dry Delivery", Univ. of Florida UF 1887 (1998).

A further suitable delivery system employs Large Porous Particles as disclosed by David A. Edwards et al. in "Large Porous Particles for Pulmonary Drug Delivery" (Science, 20. Jun. 1997, Vol. 276, p 1868-1871).

Preferred anti-inflammatory agents comprise antiseptic agents, antibiotics, corticosteroids and wound-healing promoting agents, as single substances or in combination with each other.

Preferred antiseptic agents comprise the well-known pharmaceutical substances providing fast effect, a broad range of activity, low systemic toxicity and good tissue compatibility. They can e.g. be selected from the group comprising metal compounds, phenolic compounds, detergents, iodine and iodine complexes. A specifically preferred antiseptic agent is povidone iodine.

Preferred agents promoting the healing of wounds comprise substances which have been described in the literature for such application. Preferred such agents include substances known to promote epithelisation. These include vitamins, specifically from the vitamin B group, allantoin, some azulenes etc.

Some presently highly preferred embodiments of the invention comprise anti-inflammatory agents or combinations of such agents which show beneficial effects in tissue repair, especially with respect to functional and cosmetic tissue remodelling. In these embodiments, the active agent is often an antiseptic, such as PVP-iodine, or an antibiotic.

In preferred embodiments, the invention's preparations containing anti-inflammatory, especially antiseptic and/or wound-healing promoting agents can comprise further agents such as anaesthetic agents. Inventive preparations can also contain customary further agents, including adjuvants and additives, antioxidants, conserving agents or consistency-forming agents such as viscosity adjusting additives, emulgators etc.

Generally, the concentrations in the preparation, particle sizes, active agent loadings etc. will be selected for such alternative carriers to correspond basically to the parameters discussed herein with respect to liposome preparations. Selecting and providing such parameter based inter alia on straightforward experimentation, is well within the skill of an ordinary worker experienced in this art.

A presently highly preferred use of the inventive liposome preparations is in the local treatment of infections of the nose, mouth and throat, especially when the liposome preparations contain povidone iodine. Also in this indication, the inventive antiseptic preparations, especially those containing PVP iodine, have the great advantage of not causing resistances and lead to much less allergic reactions, while permitting a very cost-efficient therapy with a broad spectrum of effect. A povidone iodine liposome preparation according to this invention is e.g. effective against viruses, such as herpes simplex. This effect is not provided by antibiotic agents. Further, a liposome preparation of a microbicidal agent such as povidone iodine provides protracted release of the agent from liposomes in the nasal or oral mucosa. This leads to extended effect of the antimicrobial substance, and thus less frequent application, as compared with the customary antiseptic solution preparations.

The present invention is also useful in the treatment of infectious diseases or for alleviation of diseases such as HIV infections which are accompanied by opportunistic infections. Also patients having a suppressed immune system, for example, after organ transplants, can be treated according to the invention. In particular, acute and chronical laryngopharyngitis and angina can be treated with the povidone iodine preparation according to the invention.

Further highly preferred use is in tissue repair, especially in functional and cosmetic tissue remodelling.

Preparations according to this invention can take a variety of forms, which are suitable for administration via the upper respiratory tract and the ear, including pharmaceutically acceptable solid or liquid formulations. Preparations according to this invention can be therefore in the form of (powder) aerosol or in the form of a compacted solid medicament reservoir, preferably a ring tablet, more preferably a gelatine capsule, a powder, a spray, an emulsion, a dispersion, a suspension or a solution containing the carrier and agent or agents. They can be in the form of a gel, or some other semi-solid, viscous or solid application form, e.g. for application in the mouth cavity.

Generally, the amount of active agents in an inventive preparation will be determined by the desired effect, on the one hand, and the carrying capacity of the carrier preparation for the agent, on the other hand.

For inventive preparations with large amounts of active agents or high dosages of active agent, solid, liquid or gel preparations are often preferred to nebulized preparations or aerosols, or to powders or powder aerosols. Broadly, the amount of active agent in an inventive carrier preparation can range in concentrations between the lower limit of effectiveness of the agent and the maximum loading of the agent in the respective carrier preparation.

More specifically, for an antiseptic agent, such as povidone iodine, a solution or dispersion in an inventive carrier preparation, especially where the carrier is a liposome preparation, can contain between 0.1 and 10 g of agent in 100 g of preparation. Such a preparation will then typically contain between 1 and 5 g of liposome membrane-forming substance, especially lecithin, per 100 g of preparation.

In a lotion, which can be a hydrophilic or a lipophilic lotion, a typical range of active agent will be between 0.5 and 10 g agent, and between 1 and 5 g, preferably about 4 g of liposome membrane forming agent such as hydrogenated soy bean lecithine, per 100 g of lotion. In the case of a hydrophilic lotion, electrolyte solution will often be used in preparing the liposome containing lotion. A lipophilic lotion will often be made from agent, membrane forming substance and lipophilic formation agents such as medium chain length triglycerides etc.

A hydrophilic cream comprising an inventive liposome preparation will generally comprise between 0.1 and 10 g agent, such as povidone iodine, together with between about 1 and 10 g membrane forming substance and further typical O/W cream forming additives, per 100 g of cream.

A comparable amphiphilic cream according to the invention will have similar contents of agent and membrane forming substance such as lecithine, and will have the typical further additives of an amphiphilic cream.

A hydrophilic ointment according to the invention can broadly comprise between 0.1 and 10 g agent and between 1 and 10 g liposome membrane forming substance such as lecithine, together with typical prior art ointment basis substances such as Macrogol™ and water, in 100 g of ointment.

A non-alcoholic hydrogel according to the invention could broadly comprise between 1 and 5 g agent such as povidone iodine, approximately 2 g lecithine and gel forming substances such as Carbopol™, with pH-adjusting agent and water to form 100 g of hydrogel.

An inventive aerosol or spray preparation will often comprise up to 50 mg, but could comprise up to and above 100 mg of liposomal active agent formulation, per unit spray dose. The spray preparation will typically comprise at least 10% wt of active agent such as PVP-Iodine in the loaded liposomes (or alternative carrier particles), but may comprise up to 50% wt or even more of active agent. Where the active agent is PVP-Iodine, the amount of available iodine will generally be about 10% wt (based on PVP-Iodine).

More specific formulations are notable from the embodiment examples.

The features and advantages of this invention will become notable in more detail from the ensuing description of preferred embodiments. In these embodiments which include a best mode, povidone iodine is exemplified as an antiseptic agent and liposomes are chosen as the carrier. This should, however, not be construed as a restriction of this invention to antiseptic agents or, among antiseptic agents, to povidone iodine, and/or to liposomes as the carrier, although such preparations are specifically preferred.

One preferred method for producing the invention's liposomes can generally be described as follows:

The lipid membrane-forming components, e.g. lecithine, are dissolved in a suitable solvent such as chloroform or a 2:1 mixture of methanol and chloroform and are filtered under sterile conditions. Then, a lipid film is produced on a sterile high surface substrate, such as glass beads, by controlled evaporation of the solvent. In some cases, it can be quite sufficient to form the film on the inner surface of the vessel used in evaporating the solvent, without using a specific substrate to increase the surface.

An aqueous system is prepared from electrolyte components and the (one or more) active agents to be incorporated in the liposome preparation. Such an aqueous system can e.g. comprise 10 mmol/l sodium hydrogen phosphate and 0.9% sodium chloride, at ph 7.4; the aqueous system will further comprise at least the desired amount of the active agent, which in the embodiment examples is povidone iodide. Often, the aqueous system will comprise an excess amount of agent or agents.

The liposomes are generally formed by agitating said aqueous system in the presence of said film formed by the lipid components. At this stage, further additives can be added to improve liposome formation; e.g. sodium cholate can be added. Liposome formation can also be influenced by mechanical action such as pressure filtration through e.g. polycarbonate membranes, or centrifuging. Generally, the raw liposome dispersion will be washed, e.g. with electrolyte solution as used in preparing the above-described solution of the active agent.

When liposomes with the required size distribution have been obtained and washed, they can be redispersed in an electrolyte solution as already described, often also comprising sugars such as saccharose or a suitable sugar substitute. The dispersion can be freeze-dried, and it can be lyophilysed. It can, prior to use, be reconstituted by addition of water and suitable mechanical agitation at the transition temperature of the lipid component, which for hydrogenated soy bean lecithine is e.g. 55° C.

In the following Examples, hydrogenated soy bean lecithine (EPIKURON™ 200 SH obtainable from Lukas Meyer, Germany or PHOSPOLIPON™ 90H obtainable from Nattermann Phospholipid GmbH, Germany) was used. However, other pharmaceutically acceptable liposome membrane forming substances can be used instead, and the person skilled in the art will find it easy to select suitable alternative liposome forming systems from what is described in prior art.

EMBODIMENT EXAMPLE I

In a 1000 ml glass flask, provided with glass beads for increased surface, 51.9 mg cholesterol and 213 mg hydrogenated soy bean lecithine were dissolved in a sufficient amount of a mixture of methanol and chloroform in a 2:1 ratio. The solvent was then evaporated under a vacuum until a film was formed on the inner surface of the flask and on the glass beads.

2.4 g PVP iodine (containing about 10% available iodine) were separately dissolved in 12 ml water.

Again in a separate vessel, 8.77 g sodium chloride and 1.78 g $Na_2HPO_4.2H_2O$ were dissolved in 400 ml water. Further water was added up to a total volume of 980 ml, and then, approximately 12 ml 1N hydrochloric acid were added to adjust pH to 7.4. This solution was then topped up with water to exactly 1000 ml.

In a fourth vessel, 900 mg saccharose and 57 mg disodium succinate were dissolved in 12 ml water.

The PVP iodine solution was then added to the lipid film in the flask and the mixture was shaken until the film dissolved. This produced liposome formation from the hydrated lipids in the flask. The product was centrifuged and the supernatant liquid was discarded. The saccharose solution was added ad 12 ml and the product was again centrifuged. Afterwards the supernatant liquid was again discarded. At this stage, a further washing step, using the saccharose solution or the sodium chloride buffer solution could be used.

After the last centrifugation step and discarding of the supernatant, sodium chloride buffer solution was added ad 12 ml, and the liposomes were homogenously distributed therein. The product was then distributed into vials each containing 2 ml liposome dispersion, and the vials were then subjected to a freeze-drying step.

After the freeze-drying, each vial comprised about 40 mg solids.

The method of Embodiment Example I has a minor disadvantage in that the PVP iodine solution used, due to the high percentage of solids, is rather viscous and thus more difficult to handle.

EMBODIMENT EXAMPLE II

In a 2000 ml flask provided with glass beads to increase surface, 173 mg hydrogenated soy bean lecithine and 90 mg disodium succinate were dissolved in approximately 60 ml of a methanol/chloroform mix in a 2:1 ratio. The solvent was removed under vacuum until a film was formed.

4 g PVP iodine (10% available iodine) were dissolved in 40 ml of the sodium chloride buffer solution described in Embodiment Example I, and were added to the lipid film in the flask. The flask was then shaken until the film dissolved and liposomes were formed.

The product was centrifuged and the supernatant liquid was discarded.

To the thus produced liposome pellet, further sodium chloride buffer solution was added ad 40 ml, and the centrifuging step was repeated. The supernatant was again discarded. At this stage, this washing step could be repeated where necessary.

After the final centrifuging and decanting step, sodium chloride buffer solution was again added to the precipitated liposomes ad 40 ml. The homogenous dispersion was then distributed into vials, each vial containing about 2 ml liposome dispersion, and the vials were then subjected to a freeze-drying step. This produced approximately 200 mg freeze-dried solids per vial.

From the freeze-dried solids of Examples I and II, further preparations were made as described in subsequent Embodiment Examples and Test Reports.

Like that of Embodiment Example I, the above-described method uses a hydrating step after film formation in the presence of organic solvents and aims at inclusion rates of 5 bis 15%. These methods generally produce rather large and often multi-lamellar liposomes.

The above-described methods can be modified by a high pressure filtering step through a suitable membrane such as a polycarbonate membrane after the raw liposomes have been formed or after any of the subsequent washing steps or directly by using high pressure homogenisation. This produces much smaller, unilamellar liposomes at increased amounts of encapsulated agent.

Instead of high pressure homogenisation, other prior art methods known to provide small uniform sized liposomes can be employed.

EMBODIMENT EXAMPLE III

A hydrophilic (O/W) cream was prepared from 10 g hydrogenated soy bean lecithine/PVP iodine liposomes as described in Embodiment Example II; these were mixed with 4 g Polysorbate 40™, 8 g cetylstearyl alcohol, 8 g glycerol, 24 g white vaseline, and water ad 100 g.

EMBODIMENT EXAMPLE IV

An amphiphilic cream was prepared from 10 g hydrogenated soy bean lecithine/povidone iodine liposomes as described in Embodiment Example II; 7.5 g medium chain length tryglyceride, 7 g polyoxyethyleneglycerol monostearate, 6 g cetylstearyl alcohol, 8 g propylene glycol, 25 g white vaseline, and water ad 100 g.

EMBODIMENT EXAMPLE V

A hydrophilic ointment which can be rinsed off with water was prepared using 10 g of liposomal PVP iodine as described in Embodiment Example II, 55 g Macrogol 400™, 25 g Macrogol 4000™, and water ad 100 g.

EMBODIMENT EXAMPLE VI

A hydrogel was prepared from 4 liposomal PVP iodine as described in Embodiment Example II, 0.5 g Carbopol 980 NF™, sodium hydroxide ad pH 7, water ad 100 g.

Further modifications of the above-described embodiments are envisaged.

Thus, the creams of Embodiment Examples III and IV can have an additional content of an agent known to promote the healing of wounds, such as allantoin. Such an agent will be added in a pharmaceutically useful concentration, in the case of allantoin in the range of 0.1 to 0.5 g, per 100 g of cream. The wound-healing agent can be incorporated in the cream base, in which case it will largely be outside the liposomes. It can, however, be partly or mostly incorporated in the liposomes, in which case it will be added at a corresponding suitable stage of the liposome preparation method.

Similar alternatives are easily envisaged on the basis of the further Embodiment Examples.

It is also possible to prepare embodiments similar to the above described ones, which comprise an agent capable of promoting the healing of wounds instead of, and not in addition to, the antiseptic agent as e.g. povidone iodine disclosed in the above Embodiment Examples. Presently, it is however preferred to use a wound healing promoting agent (if at all) in addition to an antiseptic agent.

For application of the inventive preparations to a patient, known systems can be used, such as pneumatic pump applicators, two-chamber gas pressure packs, aerosol spray dispensers etc.

In a pneumatic pump applicator, a bellows device is provided between an upstream and a downstream valve, both valves operating one way in the same direction. A supply of pharmaceutical preparation, such as an ointment or gel, is contained in a reservoir upstream of the valves-and-bellows device.

When compressing the bellows, the downstream valve opens and permits a dosed amount of preparation to leave the device for application. When the bellows is extended, this valve shuts and prevents reentry of the preparation. At the same time, the upstream valve opens and permits preparation from the reservoir to enter into the bellows, for release through the downstream valve upon the next compression step of the bellows.

The reservoir is sealed by a closure element which can move through the reservoir like a piston moves in a cylinder. By the stepwise emptying of the reservoir, this closure element is sucked into the reservoir, so that the remaining amount of pharmaceutical preparation in the reservoir is always sealed off, while at the same time the reservoir can be emptied.

Such a device is useful for pasty preparations, creams, ointments etc.

In a two-chamber gas pressure pack, the pharmaceutical preparation is contained in a bag of flexible plastics film material. Often, this is high pressure polyethylene.

The bag is contained inside a gas tight pressure vessel which further contains a supply of pressurizing gas, very often a compressed inert gas like nitrogen or air.

The plastic film bag has only one outlet, which is gastightly connected to the interior wall of the pressure vessel, surrounding a single opening thereof. The pressurized gas in the vessel tends to compress the bag, driving the pharmaceutical preparation inside the bag out through the opening of the bag and thus through the opening of the vessel. A valve and, in case, spray-head device is provided in the vessel mouth. Operating the valve releases a spray mist, a jet of liquid or a portion of flowable solid such as cream. Using such a system, solutions, emulsions, creams, ointments and gels can be dosed and applied.

Using inventive preparations efficiency tests were then carried out, as follows:

Test I

This was an in-vitro-test of the bactericidal effect provided by an inventive povidone iodine liposome preparation. The test was based on the quantitative suspension test as described in "Richtlinien der Deutschen Gesellschaft für Hygiene und Mikrobiologie", 1989. In this test, the bactericidal agent is used to kill *staphylococcus aureus* (ATCC 29213), a major problem in hospital hygiene.

The liposome preparation used was that of Embodiment Example I. At different contact times between 1 and 120 minutes, the minimum concentration of the preparation in water was determined which was capable of killing the staphilococci.

The results are shown in Table 1.

TABLE I

| Contact Time (Minutes) | Bactericidal Concentration |
| --- | --- |
| 1, 2, 3, 4 | ≧0.060% |
| 5, 30, 60 | ≧0.015% |
| 120 | ≧0.007% |

The results show that at short contact times (between 1 and 4 minutes) the bactericidal concentration is as low as 0.06% and that at long contact times (120 minutes) the bactericidal concentration can be as low as 0.007%.

Test II

The virucidal and chlamydicidal activity of liposomal PVP-iodine has been studied, in cell cultures, by Wutzler et al., 9th European Congress for Clinic Microbiology and Infection Diseases, Berlin, March 1999. In cell cultures, liposomal PVP-iodine is highly effective against herpes simplex virus type 1 and adenovirus type 8, while the long-term cytotoxicity experiments indicated that the liposomal form is better tolerated than aqueous PVP-iodine by the majority of cell lines tested. PVP-iodine in liposomal form is not genotoxic.

Test III

A 3% PVP-iodine hydrogel liposomal preparation was compared with a 3% PVP-iodine ointment, where the active agent was not in liposomal form. The agent was applied to standardized in vitro cultures of rat skin and peritoneal explants, as a screening for tissue compatibility of skin and wound antiinfectives.

The growth rate of the cultured explants was studied after 30 minutes exposure and incubation with a test substance.

Again, the substantially better toleration of the liposomal preparation was clearly shown in the results, in terms of peritoneum growth rate and skin growth rate.

With the ointment, the peritoneum growth rate reached 85%, and the skin growth rate reached 90%; with the liposomal hydrogel formulation, the peritoneum growth rate was 96%, and the skin growth rate was 108%; these values are to be compared with 100% values in a control test using Ringer's solution as the agent.

Test IV

The toleration of liposomal PVP-iodine solutions for nasal applications was studied by investigating the influence of different test substances on ciliated epithelium cells, the most sensible cells of the mucous membrane. A cytotoxic damage of these cells which would cause a restriction of the mucociliar clearance can be determined by a detectable decrease of the ciliary vibration.

Human ciliated epithelium cells were analysed by an in-vitro method which enables the determination of the ciliary activity or ciliary vibration. The corresponding cells were exposed and incubated with 100 μl test substance at a temperature of 37° C. After an incubation period of 5 minutes the ciliary vibration was measured.

By using this in-vitro method a nutriant solution (Dulbeco) as standard, a 0.2% chlorohexidine solution (typical antiseptic agent), conventional polyvidone iodine solutions (Betaisodona®) of different concentrations (5.0%, 2.5% and 1.25% PVP-iodine) and a liposomal solution containing 4.5% of PVP-iodine were tested.

The substantially better toleration of the liposomal preparation was clearly shown in the results: if the ciliated epithelium cells were exposed to the Betaisodona solutions containing 5.0% or 2.5% PVP-iodine, no ciliary activity could be observed after the incubation period. Treating the cells with a chlorohexidine solution led to a decrease of the measured ciliary vibration in comparison to the standard (nutriant solution). The low concentrated Betaisodona solution containing 1.25% PVP-iodine, didn't cause a detectable decrease of the ciliary activity. With respect to the measured ciliary vibration no differences to the standard (nutrian solution) could be determined by exposing the human ciliated epithelium cells to the concentrated liposomal 4.5% PVP-iodine solution.

These results indicate that the liposomal formulation is well tolerated for nasal application and advantageous with respect to for e.g. chlorohexidine or conventional Betaisodona solutions.

The invention claimed is:

1. A method for suppressing undesired tissue formation or for restoring the original appearance of tissue at a site of tissue damage in the upper respiratory tract or ear of a patient comprising, administering to a patient in need thereof at the site of tissue damage, an amount of liposomes sufficient to suppress undesired tissue formation or to restore the original appearance of the tissue, said liposomes containing povidone iodine.

2. The method of claim 1, wherein the liposomes further contain an anti-inflammatory agent.

3. The method of claim 1, wherein the liposomes further contain another agent that promotes granulation or epithelialization.

4. The method of claim 1, wherein the liposomes further contain an anesthetic.

5. The method of claim 1, wherein the liposomes further contain a conserving agent or an antioxidant.

6. The method of claim 3, wherein the agent is dexpanthenol, allatonin, azulene, tannin, or a vitamin B compound.

7. The method of claim 1, wherein the liposomes have a diameter in the range from about 1 nm to about 20,000 nm.

8. The method of claim 1, wherein the liposomes have a diameter in the range from about 50 nm to about 4,000 nm.

9. The method of claim 1, wherein the liposomes have a diameter in the range from about 500 nm to about 2,500 nm.

10. The method of claim 1, wherein the liposomes have a diameter of about 1,000 nm.

11. The method of claim 1, wherein the liposomes comprise a liposome membrane forming substance that is present in an amount between about 1% to about 10%, by weight, of the liposomes.

12. The method of claim 11, wherein the liposomes comprise a liposome membrane forming substance that is present in an amount between about 1% to about 5%, by weight, of the liposomes.

13. The method of claim 12, wherein the liposomes comprise a liposome membrane forming substance that is present in an amount of about 4%, by weight, of the liposomes.

14. The method of claim 1, wherein the liposomes are lecithin liposomes.

15. The method of claim 14, wherein the lecithin liposomes are hydrogenated soy bean lecithin liposomes.

16. The method of claim 1, wherein the liposomes contain about 0.1% to about 10% by weight povidone iodine.

17. The method of claim 1, wherein the liposomes contain about 3% by weight povidone iodine.

18. The method of claim 1, wherein the liposomes contain about 4.5% by weight povidone iodine.

19. The method of claim 1, wherein the liposomes further contain an antibiotic.

20. The method of claim 1, wherein the liposomes further contain a corticosteroid.

21. The method of claim 1, wherein the patient is a human patient.

22. The method of claim 1, wherein the site of tissue damage is in the larynx.

23. The method of claim 1, wherein the site of tissue damage is in the middle ear.

24. A method for suppressing scar formation at a site of tissue damage in the upper respiratory tract or ear of a patient comprising, administering to a patient in need thereof at the site of tissue damage, an amount of liposomes sufficient to suppress scar formation, said liposomes containing povidone iodine.

25. A method for suppressing undesired tissue formation or for restoring the original appearance of tissue at a site of tissue damage in the ciliary epithelial tissues in the upper respiratory tract or ear of a patient comprising, administering to a patient in need thereof at the site of tissue damage, an amount of liposomes sufficient to suppress undesired tissue formation or to restore the original appearance of the tissue, said liposomes containing povidone iodine.

* * * * *